US010953176B2

(12) United States Patent
Cupelli et al.

(10) Patent No.: US 10,953,176 B2
(45) Date of Patent: Mar. 23, 2021

(54) ASSEMBLY FOR INTUBATION

(71) Applicant: North American Rescue, LLC, Greer, SC (US)

(72) Inventors: Matt Cupelli, Greer, SC (US); Brent Bronson, Duncan, SC (US); Scott Bolleter, San Antonio, TX (US)

(73) Assignee: North American Rescue, LLC, Greer, SC (US)

(*) Notice: Subject to any disclaimer, the term of this patent is extended or adjusted under 35 U.S.C. 154(b) by 1037 days.

(21) Appl. No.: 15/435,102

(22) Filed: Feb. 16, 2017

(65) Prior Publication Data

US 2017/0232217 A1 Aug. 17, 2017

Related U.S. Application Data

(60) Provisional application No. 62/295,831, filed on Feb. 16, 2016.

(51) Int. Cl.
*A61M 16/04* (2006.01)
*A61M 16/06* (2006.01)
*A61M 16/08* (2006.01)

(52) U.S. Cl.
CPC .... *A61M 16/0488* (2013.01); *A61M 16/0429* (2014.02); *A61M 16/0434* (2013.01); *A61M 16/0816* (2013.01); *A61M 16/0683* (2013.01); *A61M 2205/586* (2013.01); *A61M 2209/06* (2013.01)

(58) Field of Classification Search
CPC .......... A61M 16/0429; A61M 16/0434; A61M 16/0465; A61M 16/0488; A61M 16/0683; A61M 16/0816; A61M 2205/586; A61M 2209/06

USPC ......................................................... 606/196
See application file for complete search history.

(56) References Cited

U.S. PATENT DOCUMENTS

| 4,643,188 A | 2/1987 | Weiss |
| 5,681,323 A | 10/1997 | Arick |
| 2010/0307489 A1 | 12/2010 | Harms |
| 2012/0247477 A1* | 10/2012 | Stephenson ....... A61M 16/0816 128/207.14 |
| 2014/0128902 A1* | 5/2014 | Guerra ............... A61M 16/0447 606/196 |

(Continued)

OTHER PUBLICATIONS hitecmed website for Endotracheal Tube Introducer, captured from Internet Archive on Mar. 7, 2015 (Year: 2015).*

*Primary Examiner* — Timothy A Stanis
*Assistant Examiner* — Charles M Vivian
(74) *Attorney, Agent, or Firm* — Dority & Manning, P.A.

(57) ABSTRACT

An assembly for intubation, as provided herein, may include a cricothyroidotomy tube that can receive a malleable bougie allowing the cricothyroidotomy tube to take the shape of the bougie so that the cricothyroidotomy tube can be placed in a patient. A guide device can receive the bougie so that the bougie can be manipulated with the guide device to assist with insertion of the cricothyroidotomy tube in the patient. A bougie opening can be defined in the guide device for receiving a proximal end of the bougie to position the proximal end out of the way of a care giver to reduce interference that can be caused by the proximal end. Markings on the bougie can illustrate where to position the bougie to allow a predetermined amount of the bougie to extend from the cricothyroidotomy tube.

19 Claims, 6 Drawing Sheets

(56) References Cited

U.S. PATENT DOCUMENTS

2018/0169364 A1\* 6/2018 Jeffrey .............. A61M 16/0488

\* cited by examiner

ASSEMBLY FOR INTUBATION

CLAIM OF PRIORITY

This application claims priority of U.S. Provisional Patent Application 62/295,831 filed Feb. 16, 2016 titled IMPROVED ASSEMBLY FOR INTUBATION.

BACKGROUND OF THE INVENTION

1. Field of the Invention

This invention is directed to an improved assembly for oral tracheal, intubation, positioning member assisted, or guided intubation, and surgical cricothyrotomy tube placement.

2. Description of the Related Art

There remains an increased focus on preventable causes of death in both combat and civilian settings. These preventable causes include compressible hemorrhage, traumatic airway obstruction, and tension pneumothorax. This focus results from the desire to realistically avoid such preventable deaths in both of these environments. One area that has been identified as a cause of preventable death is airway and ventilation compromise and/or obstruction.

One procedure proven to alleviate an obstructed or compromised airway is the surgical cricothyroidotomy. The surgical cricothyroidotomy is predicated, and relies upon, the proper placement of a specialized endotracheal tube in a precise location. The tube placement can be assisted by the use of a bougie, specialized intubating tube or other guide that can be used in conjunction with intubation tube. For example, United States Patent Application 2010/0307489 is directed to a bougie device for guiding insertion of an endotracheal tube into an airway.

Body habitus varies greatly and a need to identify, reach, place, and guide a tube, such as an endotracheal tube, through the cricothyroid membrane has proven challenging in the emergent and critical care settings. A bougie or other intubating positioning member has been shown capable of contacting tracheal rings and providing a tactile feedback to the care giver. This tracheal contact assists the provider with identification of the trachea and subsequent confirmation of proper tube placement. However, there are disadvantages that include the inability to rapidly and situationally adjust the bougie when presenting anatomy is either traumatically altered or significantly obese. Another problem stems from the bougie specialized positioning member, or guide length given that the excess proximal end can interfere with the procedure by making contact with the patient or environment (subsequently changing the tubes angle of entry), or visually impairing the provider. Additionally, in many these situations, the presence of bodily fluids, including blood, make handling the bougie difficult as it becomes slippery and challenging to grip.

In order to minimize these complications, it would be advantageous to have a intubation assembly that included the cricothyroidotomy tube with a bougie and a means to guide the bougie, and manipulate a slippery bougie so that the proximal end of the cricothyroidotomy or endotracheal tube could be placed in a proper position. It would also be advantageous to have a bougie or other device that would also secure the proximal end of a bougie specialized positioning member or guide in a rapidly adjustable position to reduce interference of the proximal end of the bougie with airway access and interfere with visual and tactile feedback to the care giver. It would also be advantageous to have an entire assembly or packaging with a small cube space or footprint given that space in the emergent or critical care setting is inherently at a premium. Bulky packaging and complex or time intensive assemblies may be suited for select hospital or medical providers but are not well suited for unstable, austere, or complex care situations. A specialized guide device that could be packaged separately for use in a variety of oral or surgical airway situations where assistance is needed would be beneficial.

One attempt to provide a suitable device to assist with intubation is shown in U.S. Pat. No. 5,681,323 directed to a criocthyroidotomy tube insertion device. The suggested force applied to insert the cricothyroidotomy tube and the protracted duration of the application of the force are predetermined to assist with insertion of the tube. However, the structure of this device does not lend itself well to unstable, austere, or complex care environments, or single use packaging, such that each provider could carry a device. Another example of a fairly bulky apparatus is shown in U.S. Pat. No. 4,643,188.

The prior solutions presented so far do not address the needs of the unstable, austere, or complex care environments such as the battle field or disaster area, provide for handling of a bougie of other assistance devices in non-hospital environments such as when blood or other bodily fluids make handling the bougie difficult or provide for a small foot print so that these devices can be carried by individuals such as warfighters and first responders. For example, it would be advantageous to provide for an improved intubation assembly that could be carried by each individual solider and suited for the war fighter trauma and environments.

Accordingly, it is an object of the present invention to provide a guide device that can temporarily be affixed to a bougie and cricothyroidotomy tube and provide structural adjustability to a proximal end of a bougie when a tube is being inserted in a patient.

It is another object of the present invention to provide for an improved assembly and packaging such that the device and needed supplies can be easily carried in a single use package with a reduced area for storage.

BRIEF SUMMARY OF THE INVENTION

The above objectives are accomplished by providing an improved system for intubation and surgical airway procedures. This invention is directed toward a specific system comprising: a tube having a specialized positioning member or guide positioning device with a preassembled bougie, specialized positioning member, or guide inserted into the proximal end of a specialized or standard endotracheal tube.

This entire assembly allows for the distal end of the bougie, specialized positioning member, or guide to extend beyond the endotracheal tube, yet be fixed and adjustable where needed. The assembly allows for improved access without obstruction, tactile confirmation of placement, and easy removal of bougie, specialized positioning member, or guide once airway placement has been assured.

The present invention can include a tube having a distal end and a connector attached to a proximal end; a positioning device that is removable and adjustable attached to the connector with the bore of the positioning device aligning with the bore of the tube; a bougie, specialized positioning member, or guide that is removable and adjustable is received by the positioning device and the tube when the positioning device is engaged with the connector such that a portion of the proximal end of the guide extends beyond the stopper and a portion of the distal end extends beyond of the distal end of the tube; and, depth as well as center line indicators are included on the guide to facilitate tube placement.

The invention can include a cricothyroidotomy tube having an endotracheal tube connector at one end and a distal tube end; a malleable bougie that can be inserted into the cricothyroidotomy tube causing the cricothyroidotomy tube to take the shape of the bougie so that the cricothyroidotomy tube can be placed in a patient; a guide device having a bore for receiving the bougie so that the bougie can be positioned along a longitudinal axis of the bougie wherein the guide device is pressure fit on the bougie so that the bougie can be manipulated with the guide device to assist with insertion of the cricothyroidotomy tube in a patient; an extension included in the guide device that can be received in the endotracheal tube connector so that the bougie is received into the guide device and cricothyroidotomy tube; a bougie opening defined in the guide device for receiving a proximal end of the bougie to position the proximal end out of the way of a care giver to reduce interference that can be caused by the proximal end; a guide device marking included on the bougie that, when aligned with a top of the guide device, indicates where the guide device should be positioned on the bougie to allow a predetermined amount of the distal end of the bougie to extend from the cricothyroidotomy tube distal tube end when the extension is received in the endotracheal tube connector; and, a package for receiving the cricothyroidotomy tube, bougie and guide device in a compact configuration.

A slot can extend from the bougie opening of the guide device to the edge of the guide device. Wings can be laterally positioned on the guide device to improve grip on the guide device. The wings can include ridges. An insert can be included on an inner surface of the bougie opening. An expanding lateral distance can be included on the guide device from the guide device distal end to a guide device top. An expanding lateral distance section can be positioned between the seal and mid-point of the guide device and a reducing lateral distance section positioned between the mid-point and guide device top. The guide device, when placed on the bougie, can be configured to provide for longitudinally slide between the guide device and the bougie without providing for radial slide between the guide device and the bougie.

BRIEF DESCRIPTION OF THE VIEWS AND DRAWINGS

The details of the present invention, both as to its structure and operation, are understood in part by study of the accompanying drawings which are referenced herein and in which like reference numerals refer to like parts and where.

DETAILED DESCRIPTION OF THE INVENTION

Figure 1:
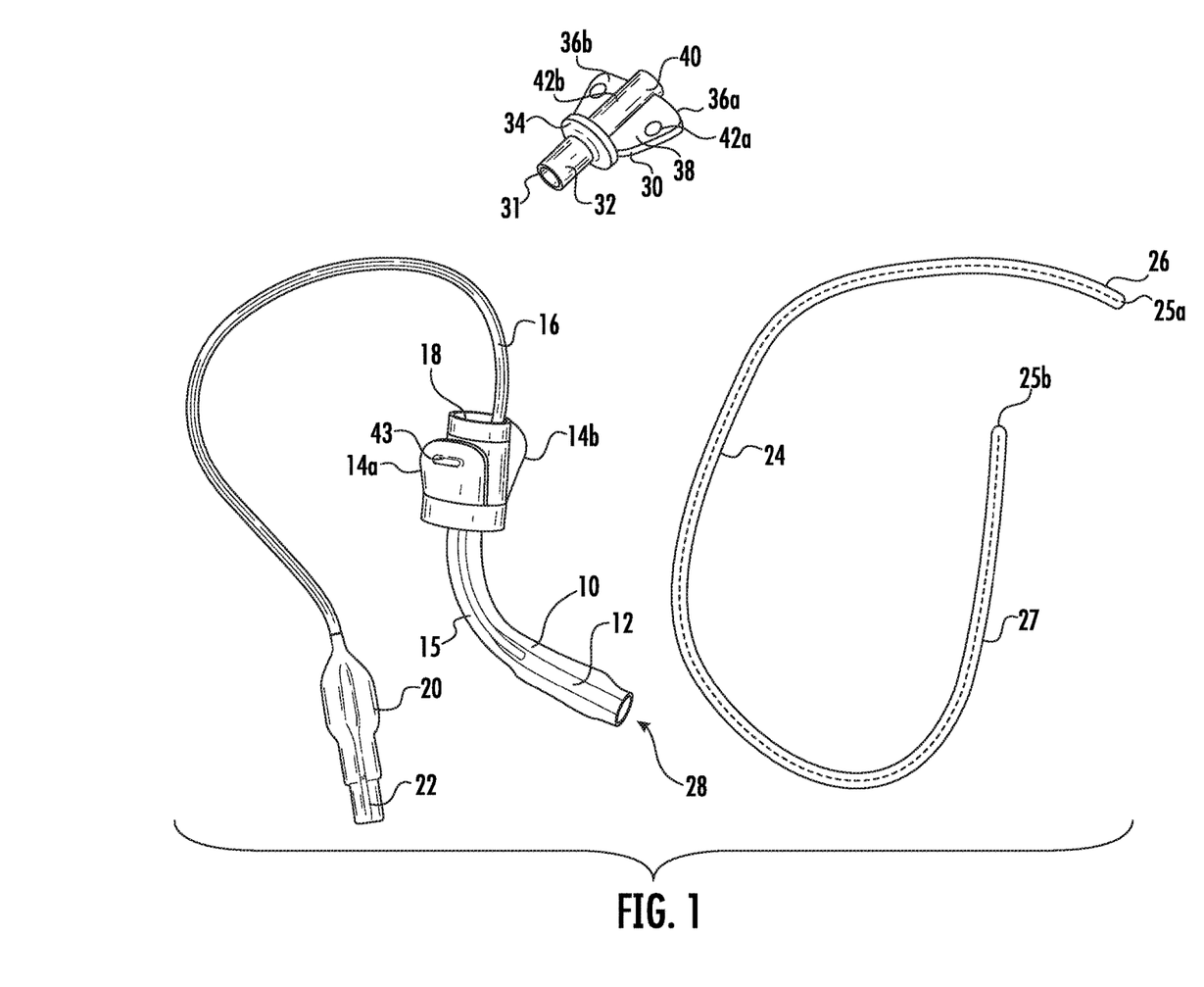
FIG. 1 is a top view of aspects of the invention.

Referring to FIG. 1, a cricothyroidotomy tube 10 having a bore, a cuff 12, endotracheal tube connector 18, inflation tube 16, connected to a pilot balloon 20 and valve 22, and securing wings 14*a* and 14*b* with securing opening 43. The cricothyroidotomy tube can include an inner cannula and an outer cannula 15, in some embodiments, and the cuff can be disposed outside the outer cannula. The bougie, a specialized positioning member or guide 24 can be a flexible, semi-flexible, or adjustable tube with rounded ends 25*a* and 25*b*. In one embodiment, the bougie includes a malleable core 27 that can be manipulated in a certain shape and maintain its shape until a predetermined amount of force is applied to the bougie.

A modified distal end 26 of the bougie can be inserted into the cricothyroidotomy tube through a guide device 30 so that bougie 24 is received in the guide device and can extend out of a guide device distal end 31. The bougie, extending sufficiently from the guide device, can be received into the cricothyroidotomy tube so that at portion of the bougie extends through the guide device and out of the distal tube end 28. The bougie can include depth and center markings along its body to indicate the position of the specialized distal end and the distance at which the bougie extends beyond the distal end of the tube when the bougie is received in the guide device. For example, the marking can indicate that a certain length of the bougie will extend out of the distal tube end when the bougie is received in the guide device and cricothyroidotomy tube and the guide device is inserted into the endotracheal tube connector.

The guide device 30 can include an extension 32 having a diameter smaller than an endotracheal tube connector to allow the guide device to be inserted into a modified or standard endotracheal tube connector. The guide device can be secured to the endotracheal tube connector by a friction fit, bayonet assembly, detent, threads, or other fastening assemblies or structures.

A seal 34 can be included adjacent to the extension such that when the positioning member is inserted into the endotracheal tube connector, the seal engages with the top of the endotracheal tube connector reducing or eliminating fluid from passing between the endotracheal tube connector and the positioning member. In one embodiment, the seal can include an annual ring extending outward from a central bore 40 and orthogonal to the central bore. The seal can include an O-ring in one embodiment.

The guide device can include lateral wings 36*a* and 36*b* adjacent to the seal, opposite to the extension, to provide a gripping surface for the bougie. Ridges 38 can be included on the wings adjacent to the central bore 40. In operation, the guide device can be used to guide the bougie to the proper location within a patient by providing a tactical and grip advantage over handling the bougie alone. The wings increase the ability to manipulate the bougie, especially radially, when attempting to insert the bougie and/or the cricothyroidotomy tube into a patient.

In one embodiment, the wings can include bougie openings 42*a* and 42*b* that can receive an end, such as a proximal end, of the bougie thereby securing the end of the bougie to the guide device. The can reduce or eliminate the free end of the bougie from interfering with the activity of the care giver, medical equipment, or other individual of object. When the bougie is secured to the guide device, it can still be rapidly adjustable, when inserting the oral endotracheal or surgical cricothyroidotomy tube, thereby reducing interference and improving functionality of the bougie, cricothyroidotomy tube, and associated treatment and equipment.

Figure 2:
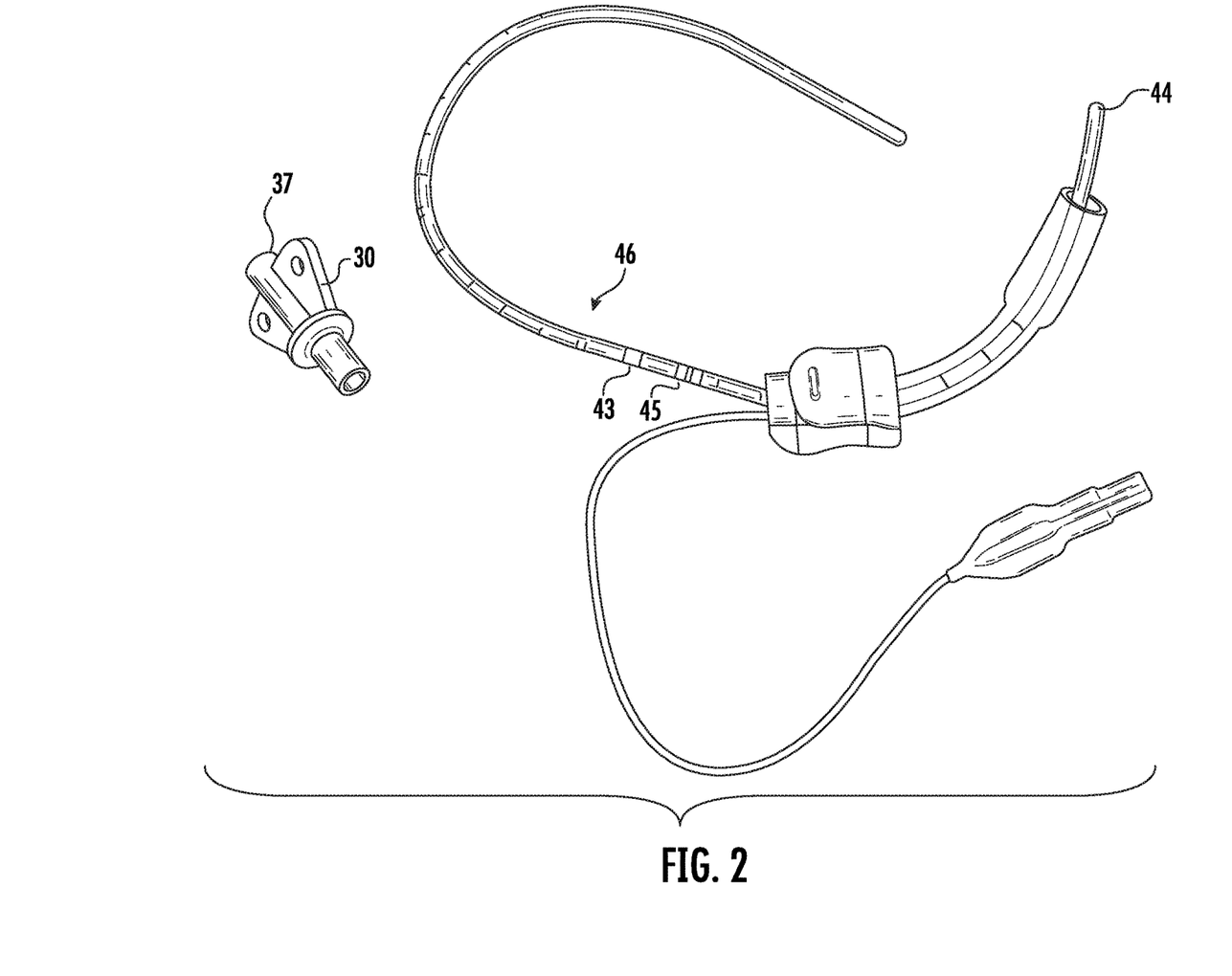
FIG. 2 is a top view of aspects of the invention.

Referring to FIG. 2, the bougie 24 is shown inserted into the cricothyroidotomy tube with a distal end 44 of the bougie extending beyond the distal end of the tube. Note that the guide device is separated from the bougie and cricothyroidotomy tube. As shown, the proximal end of the bougie extends beyond the connector potentially interfering with access to the airway. Depth indicators 46 and a centerline are positioned along the length of the bougie and indicate the amount of the bougie that extends out of the distal tube end of the cricothyroidotomy tube. In one embodiment, there is a first guide device marking 43 that indicates the position of the top 37 of the guide device when the guide device is placed on the bougie and the guide device distal end is adjacent to the endotracheal tube connector. In one embodiment, there is a second guide device marking 45 the indicates where the guide device should be positioned on the bougie to allow a predetermined amount of the distal end of the bougie to extend from the cricothyroidotomy tube distal tube end when the guide device distal end is received into the endotracheal tube connector on another case.

Figure 3:
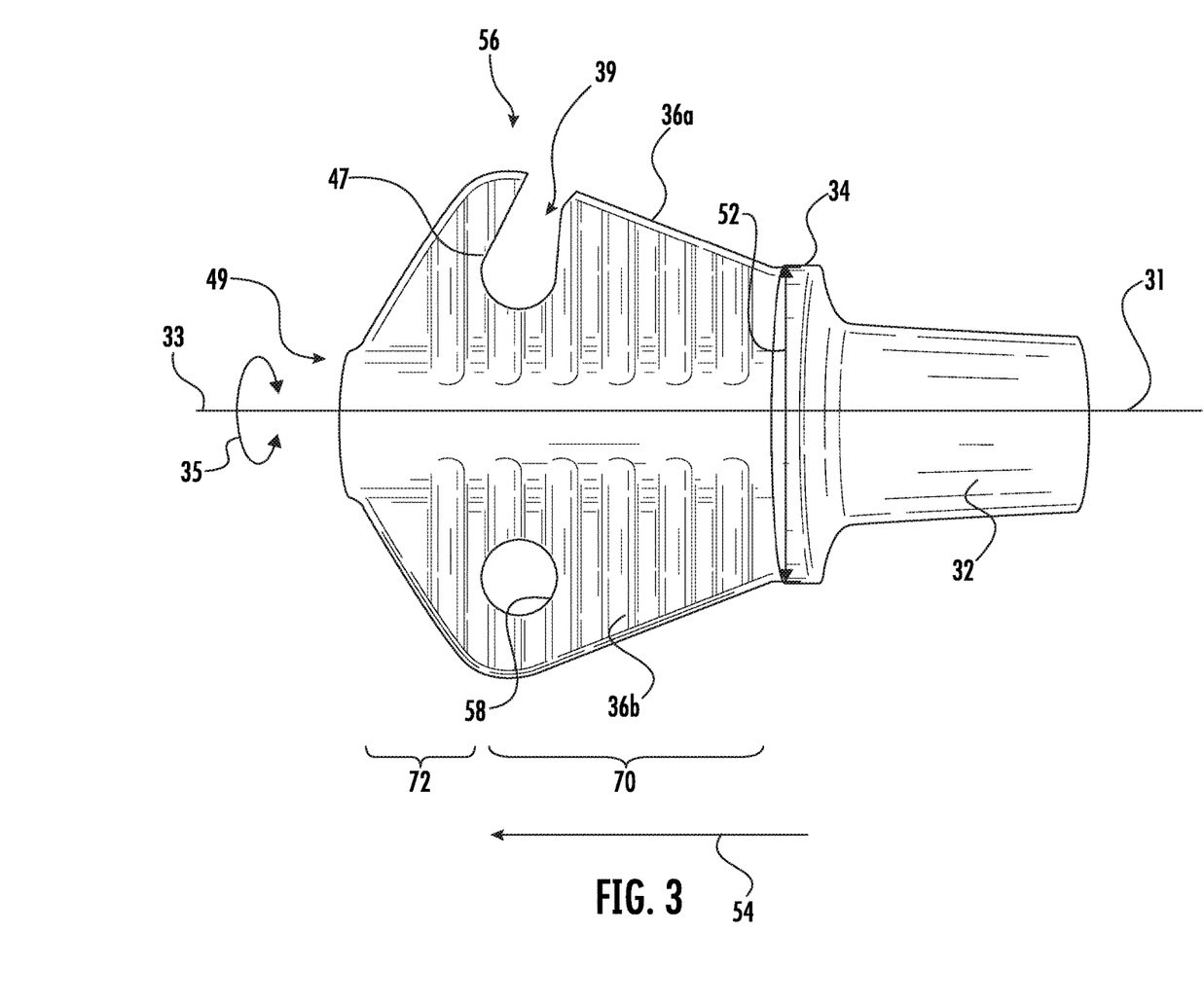
FIG. 3 is a top view of aspects of the invention.

Referring to FIG. 3, the guide device is shown in further detail. The guide device opening can include a single bougie opening 47 or bilateral bougie openings to receive and secure the proximal end of the bougie in the opening while also providing for rapid adjustment as needed. The bougie opening can include a slot 39 that extends from the bougie opening to the perimeter of the guide device. The bougie opening can have a diameter that is slightly smaller than the cross section of the bougie allowing the bougie to be friction fit into the bougie opening. The bougie can be compressible so that when it is inserted into the bougie opening, the bougie is secured to the guide device until force is applied to pull the bougie from the guide device.

The diameter of the bougie can be slightly larger than the central bore so that the bougie and guide device are cooperatively associated to provide a firm fit between the guide device and bougie so that the bougie can slide longitudinally along its long axis 33 in relation to the bougie, but not radially along path 35 so that there is no radial slide between the guide device and the bougie. The central bore diameter can be sized to accommodate the bougie and provide appropriate friction between the bougie and the guide device. The wings can include an expanding lateral distance 52 in a direction shown as 54. A expanding lateral distance section 70 can be positioned between the seal a mid-point 56. The wings can include a reducing lateral distance from the mid-point toward the guide device top 37. A reducing lateral distance section can be positioned between the expanding lateral distance section and guide device top.

The ridges can be orthogonal to the central bore in one embodiment improving the grip on the guide device when the bougie is being pulled or pushed through the guide device as well as when the guide device is being used to manipulate the position of the bougie and the cricothyroidotomy tube. In one embodiment, the bougie opening can include an insert 58 included on an inner surface of the bougie opening to assist with removably securing the bougie in the bougie opening of the guide device. In one embodiment, the positioning device includes clips, inserts, or openings that can secure the guide to the device.

Figure 4:
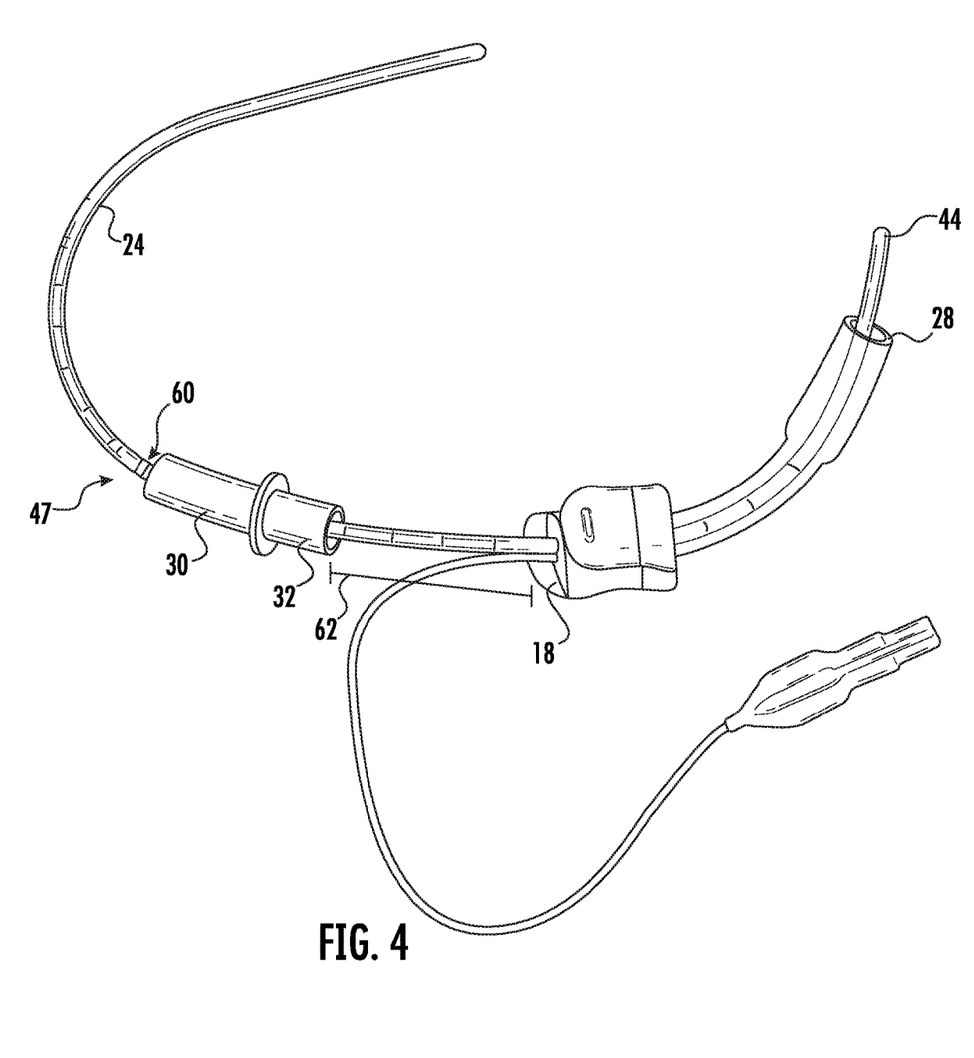
FIG. 4 is a top view of aspects of the invention.

FIG. 4 illustrates the guide device 30 placed on the bougie 24 and positioned away from the endotracheal tube connector defining a space 62 between the guide device and the endotracheal tube connector. When the guide device is placed on the bougie, the amount of the bougie that will extend from the distal tube end 28 can be known by aligning the guide device top 49 with marker 60. The markers are cooperatively associated with and related to the dimensions of the guide device, extension 32 and endotracheal tube connector 18. With this arrangement, guide device can be placed on the bougie using the depth and center indicators such that when the guide device stopper is received in the endotracheal tube connector, a predetermined length of the distal end of the bougie extends beyond of the cricothyroidotomy tube and can be used to properly position the cricothyroidotomy tube in the patient.

Figure 5:
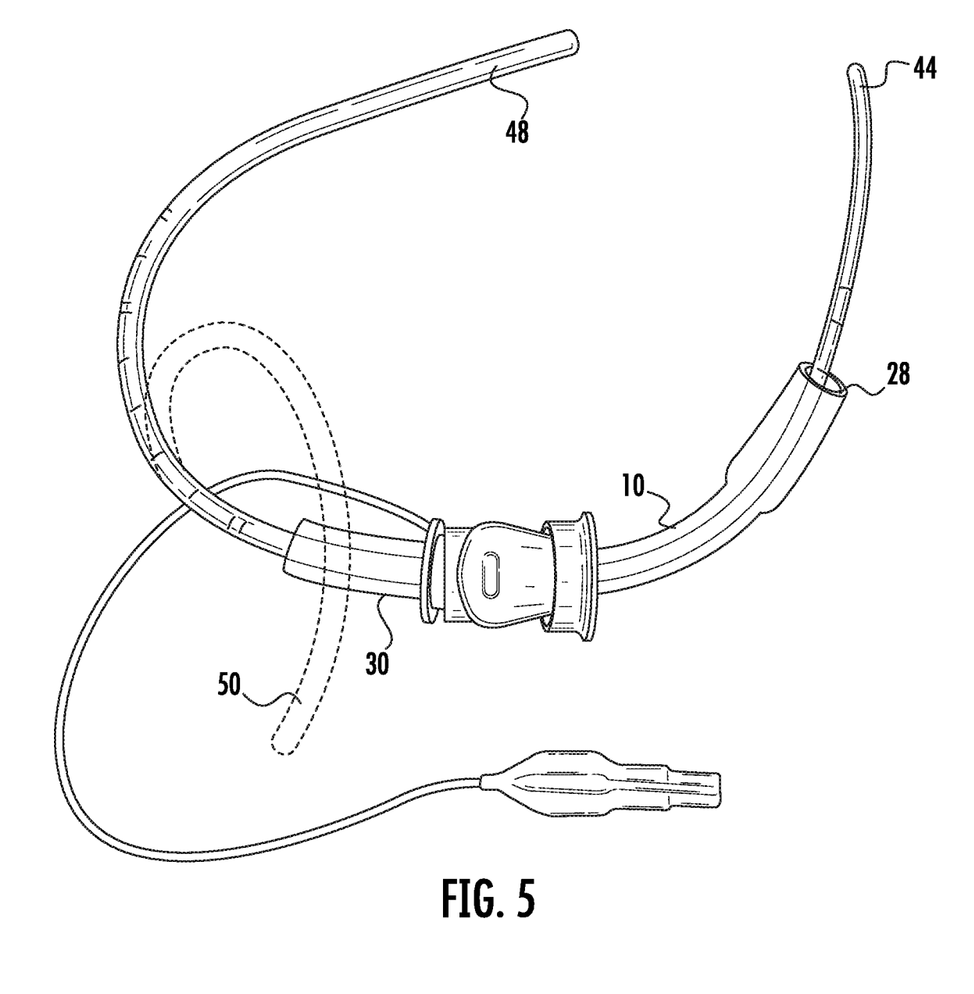
FIG. 5 is a top view of aspects of the invention; and,
FIG. 6 is a top view of aspects of the invention.

FIG. 5 shows the guide device placed on the bougie and the guide device and bougie received in the cricothyroidotomy tube. The guide device is received on in the cricothyroidotomy tube. In some cases, when the guide device is received onto the cricothyroidotomy tube with a portion of the bougie extended from the cricothyroidotomy tube, a portion of the bougie 48 can interfere with placement of other devices, procedural visualization or create other interference. When the proximal or free end 50 of the bougie is inserted into the bougie opening of the guide device the proximal end of the guide is displaced, yet adjustable and configured to facilitate access.

Figure 6:
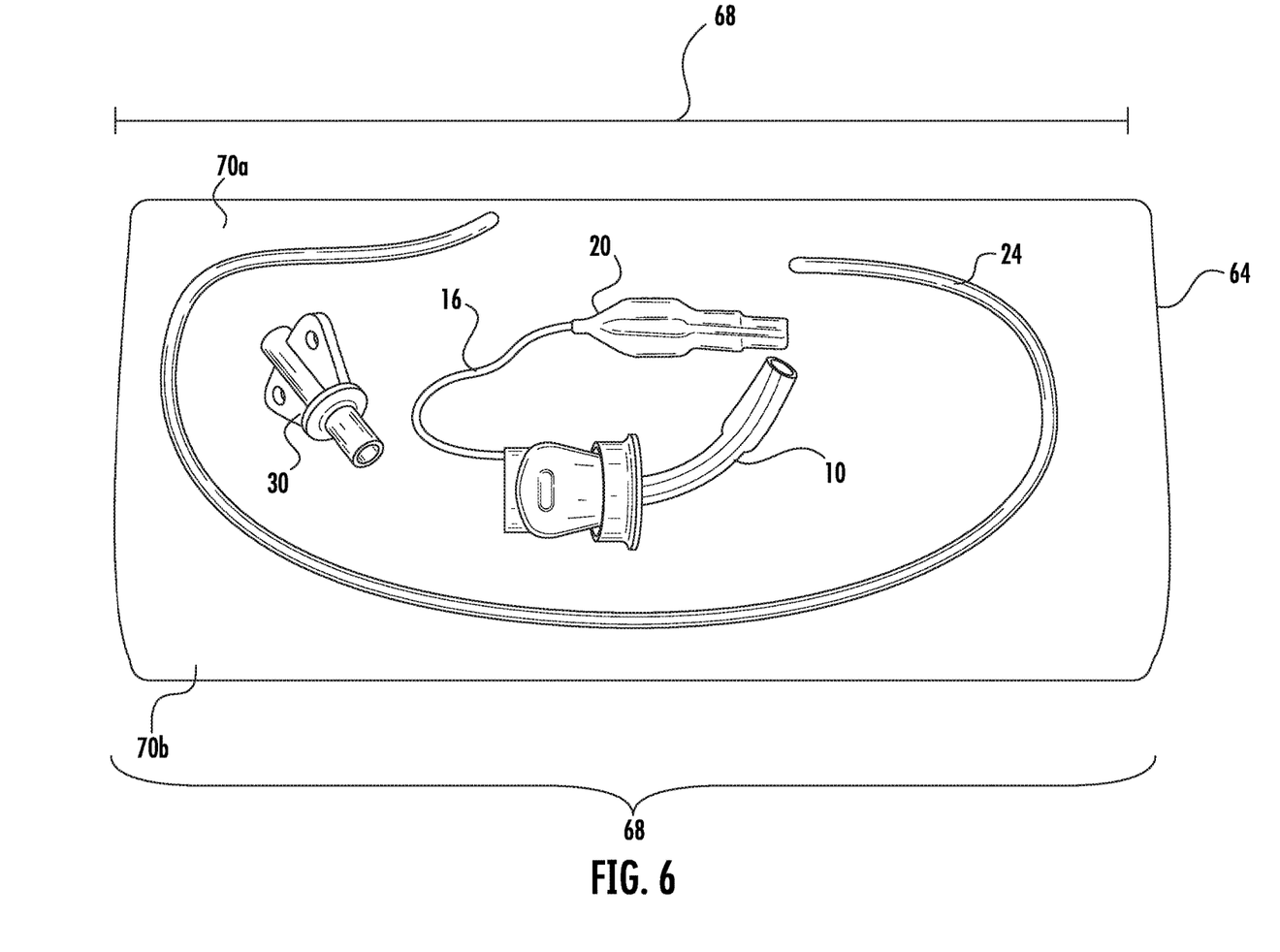

Referring to FIG. 6, the intubation assembly is shown. Individual packaging 64 is shown that can receive the cricothyroidotomy tube 10, guide device 30, bougie 24 and pilot balloon 20 with inflation tube 16 in a cavity defined in the packaging. Once the intubation assembly 66 is placed in the packaging, the packaging can be injected with an inert gas such as nitrogen to eliminate oxygen from the packaging cavity to improve shelf-live and sterility. The packaging can then be sealed through the application of heat welding, fusion, and the like. In one embodiment, the bougie is placed in a curved "C" configuration where the free ends of the bougie can be adjacent to each other. When the free ends are overlapped, the length 68 of the intubation assembly can be reduced to reduce the foot print of the packaging. The packaging can include notches 70*a* and 70*b* to assist with opening the packaging.

While the invention has been described in connection with a preferred embodiment, it is not intended to limit the scope of the invention to the particular form set forth, but on the contrary, it is intended to cover such alternatives, modifications, and equivalents as may be included within the spirit and scope of the invention as defined by the appended claims.

Unless specifically stated, terms, and phrases used in this document, and variations thereof, unless otherwise expressly stated, should be construed as open ended as opposed to limiting. Likewise, a group of items linked with the conjunction "and" should not be read as requiring that each and every one of those items be present in the grouping, but rather should be read as "and/or" unless expressly stated otherwise. Similarly, a group of items linked with the conjunction "or" should not be read as requiring mutual exclusivity among that group, but rather should also be read as "and/or" unless expressly stated otherwise.

Furthermore, although items, elements, or components of the disclosure may be described or claimed in the singular, the plural is contemplated to be within the scope thereof unless limitation to the singular is explicitly stated. The presence of broadening words and phrases such as "one or more," "at least," "but not limited to", or other like phrases in some instances shall not be read to mean that the narrower case is intended or required in instances where such broadening phrases may be absent.

What is claimed is:
1. An improved assembly for intubation comprising:
   a cricothyroidotomy tube having an endotracheal tube connector at one end and a distal tube end;
   a malleable bougie selectively inserted into the cricothyroidotomy tube causing the cricothyroidotomy tube to take the shape of the bougie to place the cricothyroidotomy tube in a patient;
a guide device having a bore extending along a longitudinal axis from a top end to a distal end, the bore selectively receiving the bougie along the longitudinal axis, wherein the guide device is pressure fit on the bougie to manipulate the bougie with the guide device to assist with insertion of the cricothyroidotomy tube in the patient;
an extension included in the guide device, the extension being selectively received in the endotracheal tube connector so that the bougie is received into the guide device and cricothyroidotomy tube;
a bougie opening defined in the guide device for receiving a proximal end of the bougie to position the proximal end out of the way of a care giver to reduce potential interference caused by the proximal end;
a guide device marking included on the bougie that, when aligned with a top of the guide device, indicates where the guide device should be positioned on the bougie to allow a predetermined amount of the distal end of the bougie to extend from the cricothyroidotomy tube distal tube end when the extension is received in the endotracheal tube connector; and,
a package for receiving the cricothyroidotomy tube, bougie and guide device in a compact configuration,
wherein the bougie opening is spaced apart in fluid separation from the bore and the cricothyroidotomy tube, and wherein the bougie opening is defined along a direction that is non-coaxial with the longitudinal axis.

2. The assembly of claim 1 including a slot extending from the bougie opening of the guide device to an edge of the guide device.

3. The assembly of claim 1 including wings laterally positioned on the guide device to improve grip on the guide device.

4. The assembly of claim 3 including ridges disposed on the wings.

5. The assembly of claim 3 including an insert included on an inner surface of the bougie opening.

6. The assembly of claim 3 including an expanding lateral distance from guide device distal end to a guide device top.

7. The assembly of claim 3 including an expanding lateral distance section positioned between a seal and a mid-point of the guide device and a reducing lateral distance section positioned between the mid-point and a guide device top.

8. The assembly of claim 1 wherein the guide device, when placed on the bougie, is configured to provide for longitudinal slide between the guide device and the bougie without providing for radial slide between the guide device and the bougie.

9. An improved assembly for intubation comprising:
a tube having a tube connector at one end and a distal tube end;
a bougie selectively inserted into the tube causing the tube to take the shape of the bougie to place the cricothyroidotomy tube in a patient;
a guide device having a bore extending along a longitudinal axis from a top end to a distal end, the bore selectively receiving the bougie along the longitudinal axis wherein the guide device is pressure fit on the bougie to manipulate the bougie with the guide device to assist with insertion of the cricothyroidotomy tube in the patient;
a bougie opening defined in the guide device for receiving a proximal end of the bougie to position the proximal end to reduce interference caused by the proximal end hanging free; and,
a guide device marking included on the bougie that, when aligned with a top of the guide device, indicates where the guide device should be positioned on the bougie to allow a predetermined amount of the distal end of the bougie to extend from the tube distal tube end when the extension is received in the tube connector,
wherein the bougie opening is spaced apart fluid separation from the bore and the cricothyroidotomy tube, and wherein the bougie opening is defined along a direction that is non-coaxial with the longitudinal axis.

10. The assembly of claim 9 including wings positioned on the guide device to improve grip on the guide device.

11. The assembly of claim 10 including ridges disposed on the wings.

12. The assembly of claim 10 including an insert included on an inner surface of the bougie opening.

13. The assembly of claim 10 including an expanding lateral distance from guide device distal end to a guide device top.

14. The assembly of claim 10 including an expanding lateral distance section positioned between a seal and a mid-point of the guide device and a reducing lateral distance section positioned between the mid-point and a guide device top.

15. The assembly of claim 9 wherein the guide device, when placed on the bougie, is configured to provide for longitudinal slide between the guide device and the bougie allowing the bougie to be removed from the guide device without providing for radial slide between the guide device and the bougie allowing for the bougie to be manipulated by the guide device.

16. An improved assembly for intubation comprising:
a cricothyroidotomy tube having a distal tube end;
a bougie selectively inserted into the cricothyroidotomy tube and configured to assist with placement of the cricothyroidotomy tube in a patient;
a guide device having a bore extending along a longitudinal axis from a top end to a distal end, the bore selectively receiving the bougie configured to manipulate the bougie when the guide device is manipulated to assist with insertion of the cricothyroidotomy tube in the patient; and,
a bougie opening defined in the guide device for receiving a proximal end of the bougie to position the proximal end to reduce interference caused by the proximal end hanging free,
wherein the guide device comprises a wing extending laterally outward from the bore,
wherein the bougie opening is defined through the wing in fluid separation from the bore and the cricothyroidotomy tube, and
wherein the bougie opening is defined along a direction that is non-coaxial with the longitudinal axis.

17. The assembly of claim 16 including a guide device marking included on the bougie that, when aligned with a top of the guide device, indicates where the guide device should be positioned on the bougie to allow a predetermined amount of the distal end of the bougie to extend from the cricothyroidotomy tube distal tube end when the guide device is adjacent to the cricothyroidotomy tube.

18. The assembly of claim 16 including a slot extending from the bougie opening of the guide device to an edge of the guide device.

19. The assembly of claim 16 wherein the guide device, when placed on the bougie, is configured to provide for longitudinal slide between the guide device and the bougie without providing for radial slide between the guide device and the bougie.

* * * * *